(12) United States Patent
Nock

(10) Patent No.: US 12,103,807 B2
(45) Date of Patent: Oct. 1, 2024

(54) ELASTOMER THIN SLEEVE FOLDING MECHANISM

(71) Applicant: Devicor Medical Products, Inc., Cincinnati, OH (US)

(72) Inventor: Andrew P. Nock, Dayton, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 144 days.

(21) Appl. No.: 17/862,977

(22) Filed: Jul. 12, 2022

(65) Prior Publication Data

US 2022/0340390 A1 Oct. 27, 2022

Related U.S. Application Data

(63) Continuation of application No. PCT/US2021/013351, filed on Jan. 14, 2021.

(51) Int. Cl.
*B65H 45/101* (2006.01)
*A61B 46/00* (2016.01)
*A61B 46/10* (2016.01)
*B65H 20/00* (2006.01)
*B65H 20/02* (2006.01)

(52) U.S. Cl.
CPC .......... *B65H 45/101* (2013.01); *A61B 46/10* (2016.02); *A61B 46/40* (2016.02); *B65H 20/005* (2013.01); *B65H 20/02* (2013.01); *B65H 2301/4521* (2013.01)

(58) Field of Classification Search
CPC .... B65H 45/101; B65H 20/005; B65H 20/02; B65H 2301/4521; A61B 46/10; A61B 46/40
See application file for complete search history.

(56) References Cited

U.S. PATENT DOCUMENTS

| 4,104,845 | A | * | 8/1978 | Hoffmann | ............... B67B 5/032 53/49 |
| 4,260,446 | A | * | 4/1981 | Saul | ....................... B31C 11/02 156/194 |
| 4,600,371 | A | * | 7/1986 | Fresnel | ..................... B65B 9/14 53/563 |
| 4,773,127 | A | | 9/1988 | Stall | |

(Continued)

FOREIGN PATENT DOCUMENTS

| EP | 0075933 A1 | 4/1983 |
| GB | 2570514 A | 7/2019 |

OTHER PUBLICATIONS

International Search Report and Written Opinion dated Apr. 13, 2021 for Application No. PCT/US21/13351, 11 pages.

*Primary Examiner* — Thomas M Wittenschlaeger
*Assistant Examiner* — Himchan Song
(74) *Attorney, Agent, or Firm* — Frost Brown Todd LLP

(57) ABSTRACT

A folding device for placing an elastomer thin sleeve on a retainer includes a mandrel, one or more rollers, and a drive system. The mandrel is configured to translate relative to a portion of the folding device. The mandrel is adapted to releasably receive the retainer. The one or more rollers are configured to rotate relative to the mandrel. The rotation of the one or more rollers being configured to fold the sleeve onto the retainer. The drive system is configured to translate the mandrel and turn the one or more rollers.

20 Claims, 13 Drawing Sheets

(56) References Cited

U.S. PATENT DOCUMENTS

| | | | | |
|---|---|---|---|---|
| 6,684,599 | B1* | 2/2004 | Fresnel | B65C 3/065 |
| | | | | 53/64 |
| 9,809,331 | B2* | 11/2017 | Nyren | B65B 5/02 |
| 10,335,125 | B2 | 7/2019 | Robinson et al. | |
| 11,390,408 | B2* | 7/2022 | Duncan | B65B 61/06 |
| 2013/0118120 | A1* | 5/2013 | Heeman | B65B 11/00 |
| | | | | 53/399 |
| 2013/0118136 | A1* | 5/2013 | Arima | B65C 9/42 |
| | | | | 53/585 |
| 2013/0167847 | A1 | 7/2013 | Rogers | |
| 2017/0233128 | A1* | 8/2017 | Lang | B29C 65/66 |
| | | | | 156/86 |
| 2019/0112090 | A1* | 4/2019 | Vetten | B65B 61/24 |
| 2023/0312294 | A1* | 10/2023 | Tomatsu | B65H 23/32 |
| | | | | 270/1.01 |

* cited by examiner

ELASTOMER THIN SLEEVE FOLDING MECHANISM

PRIORITY

This application is a continuation of International Application No. PCT/US2021/013351, entitled "Elastomer Thin Sleeve Folding Mechanism," filed on Jan. 14, 2021, which claims priority to U.S. Provisional Application Ser. No. 62/961,356, entitled "Elastomer Thin Sleeve Folding Mechanism," filed on Jan. 15, 2020, the disclosure of which is incorporated by reference herein.

BACKGROUND

In some contexts, it may be desirable to maintain sterility of certain medical devices. In such contexts, it may also be desirable to maintain sterility of any equipment used therewith before, during or after certain mechanical procedures performed using said medical devices. For instance, certain components for use with a biopsy procedure are often sterilized prior to performing such a procedure. Meanwhile, other components may be cleaned, but not completely sterilized. Where such sterile and non-sterile components interface, challenges with maintaining sterility may arise. Thus, in some instances it may be desirable to incorporate various devices or methods into such biopsy components to maintain sterility of sterile components when interfacing with non-sterile components. Merely exemplary devices and or components to facilitate sterility are disclosed in U.S. Pub. No. 2018/0325501, entitled "Biopsy Device with Sterile Sleeve," published Nov. 15, 2018.

In one merely exemplary device for facilitating sterility between component parts, an elongated thin sleeve is used to cover one or more components of a biopsy device. Such a sleeve can be used with a retainer, sheath or other semi-rigid structure to aid with manipulation of the sleeve. This combination can be used to introduce the sleeve onto one or more components of the biopsy device by unfolding, unrolling or uncompressing the sleeve from the retainer. However, challenges may be encountered during assembly when the sleeve is folded, rolled or compressed into the retainer. Accordingly, methods and/or devices may be desirable to consistently fold, roll, or compress a thin sleeve onto a retainer would be uses un many applications.

While several systems and methods have been made and used for folding elongated thin sleeves on retainers, it is believed that no one prior to the inventor has made or used the invention described in the appended claims.

BRIEF DESCRIPTION OF THE DRAWINGS

It is believed the present invention will be better understood from the following description of certain examples taken in conjunction with the accompanying drawings, in which like reference numerals identify the same elements and in which.

Figure 1:
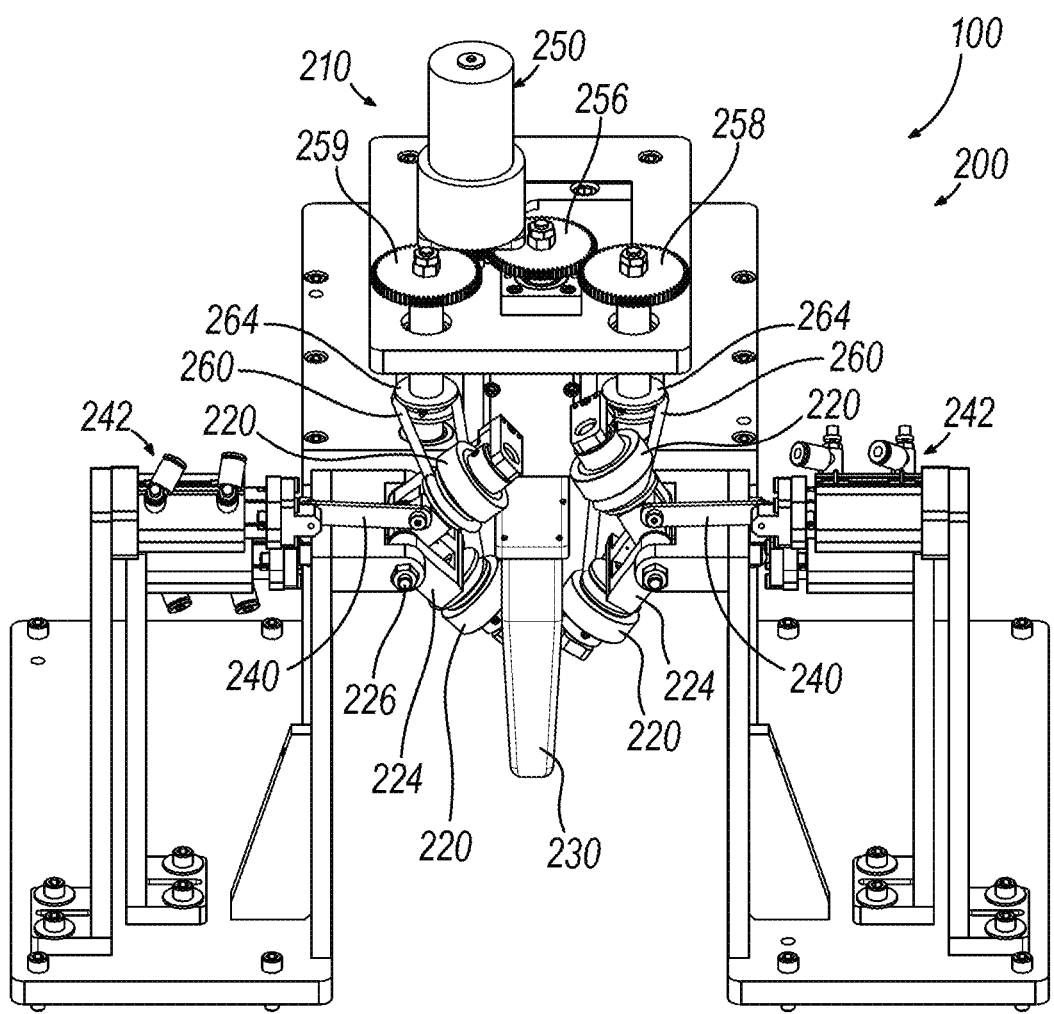
FIG. 1 depicts a front perspective view of an exemplary sleeve folding device.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION OF THE INVENTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. EXEMPLARY SLEEVE FOLDING SYSTEM

Figure 2:
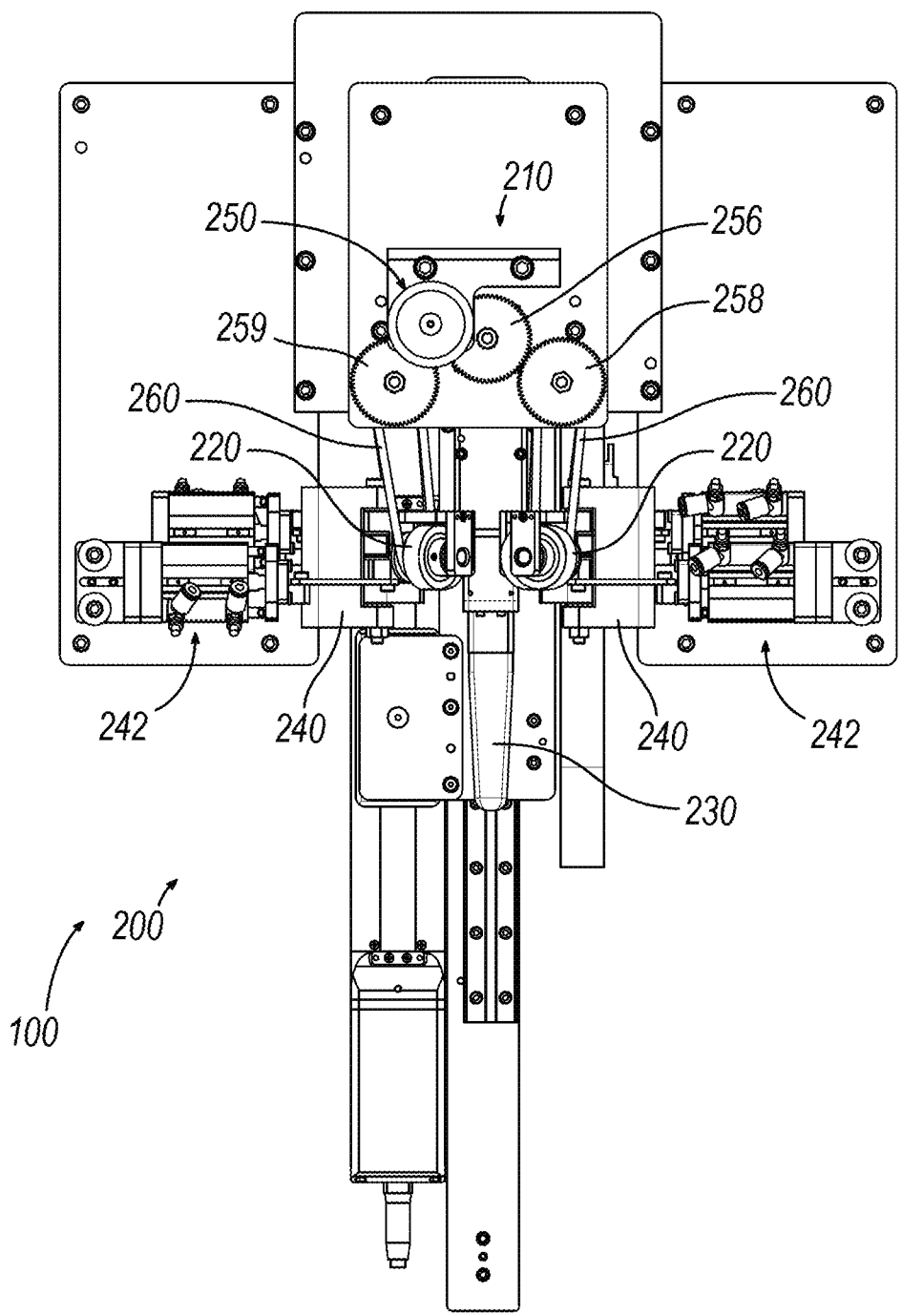
FIG. 2 depicts a top view of the sleeve folding device of FIG. 1.
Figure 3:
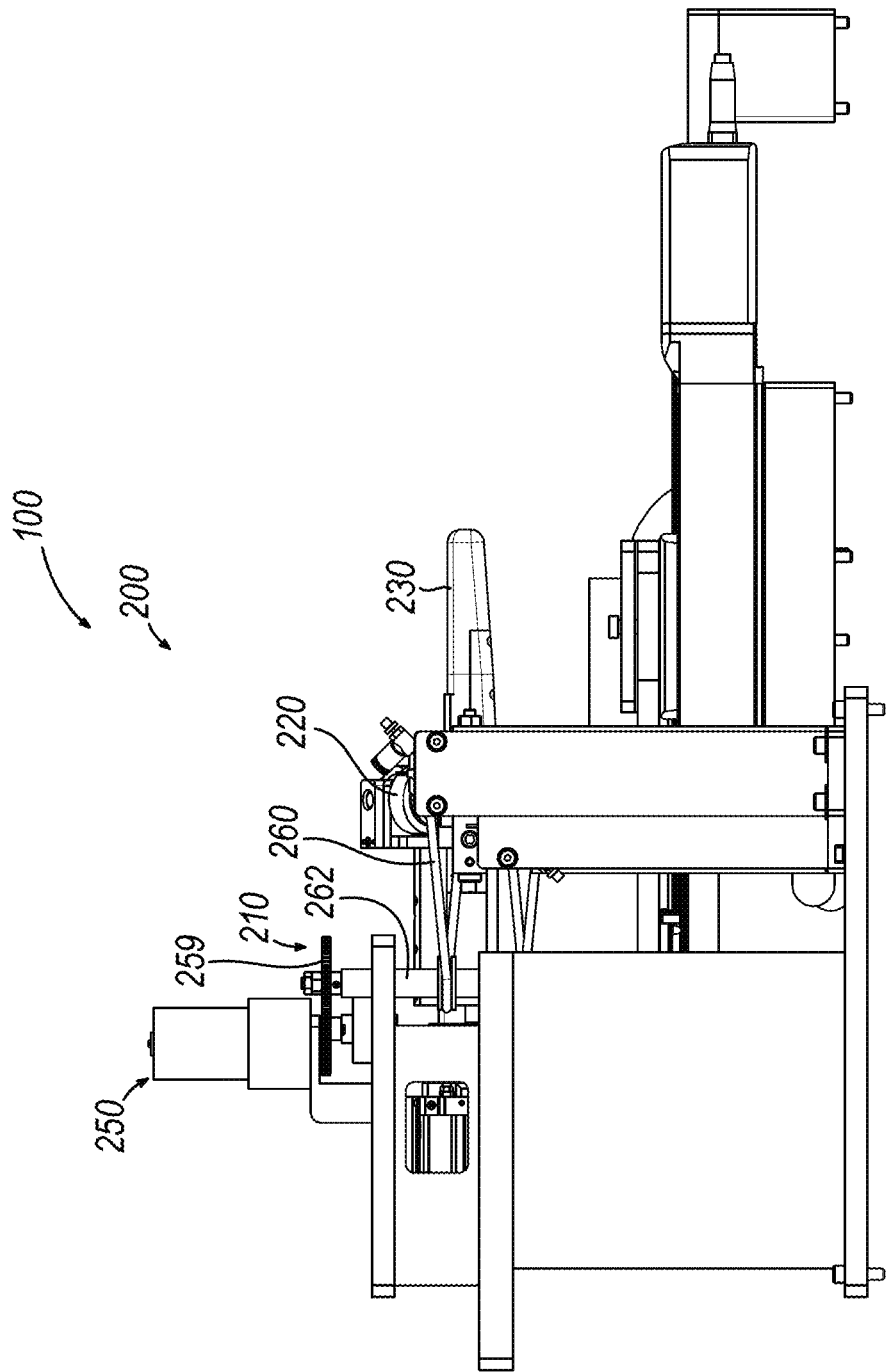
FIG. 3 depicts a side elevational view of the sleeve folding device of FIG. 1.
Figure 4:
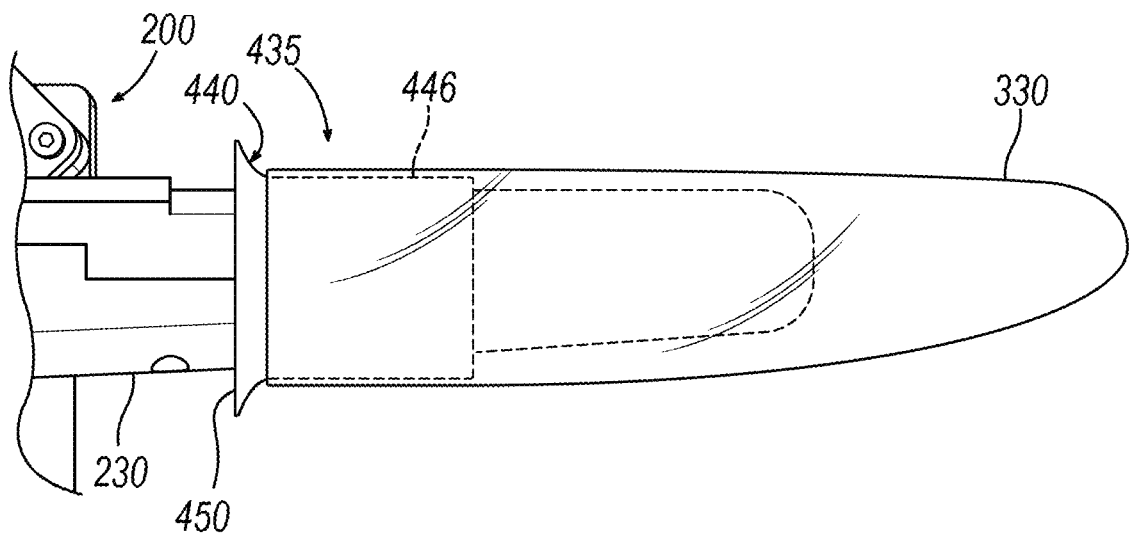
FIG. 4 depicts a side elevational view of an exemplary sleeve assembly coupled with the sleeve folding device of FIG. 1, the sleeve assembly in an extended state.

FIGS. 1 through 3 show an exemplary sleeve folding system (100) that may be used to provide sterile equipment for various applications, such as robotic end effector, dental devices, endoscopes, and biopsy devices. Folding system (100) comprises folding device (200), as well as sleeve ring (435) and sleeve (330) (Shown in FIG. 4). Folding system (100) stores sleeve (330) on sleeve ring (435). Folding device (200) include mandrel (230), one or more rollers (220), and transmission assembly (210). Mandrel (230) is configured to translate proximally and is adapted to releasably couple to sleeve ring (435). One or more rollers (220) are driven to rotate, where the rotation of one or more rollers (220) folds the cover on to sleeve ring (435). Transmission assembly (210) is configured to translate mandrel (230) and turn one or more rollers (220). Although the term transmission assembly (210) is used herein, it should be understood that in some contexts, transmission assembly (210) may be referred to as a drive system, drive assembly, transmission control, driver, and/or etc. The folds of sleeve (330) are created by applying one or more rollers (220) to slide sleeve (330) onto sleeve ring (435). At the same time, a coordinated linear motion of sleeve ring (435) moved by mandrel (230) allows for even distribution of the sleeve (330) as it folds. FIG. 4 shows sleeve ring (435) positioned on mandrel (230) of folding device (200), and unfolded sleeve (330) positioned on sleeve ring (435). It should be noted that in some embodiments the distal end of sleeve (330) is open, while in other embodiments the distal end of sleeve (330) is closed.

Mandrel (230) of folding device (200) is coupled to transmission assembly (210) and is configured to translate along the same direction as the sleeve (330) as it is folded by one or more rollers (220). In some embodiment's mandrel (230) translates in the proximal and distal directions. The coordinated linear motion of mandrel (230) with one or more rollers (220) prevents sleeve (330) from bunching as it is folded on sleeve ring (435). In other words, coordinated linear motion of mandrel (230) is configured to control the distribution of the folds in sleeve (330) created by rollers (220) by moving sleeve ring (435) relative to rollers (220). To facilitate distribution, mandrel (230) can be moved either distally or proximally. For instance, in some circumstances it may be desirable to translate mandrel (230) proximally to stack folds in sleeve (330) linearly along the length of sleeve ring (435). In other circumstances, mandrel (230) can be translated distally as sleeve (330) is folded onto sleeve ring (435), which allows for folds to develop on a more distal portion of the sleeve ring (435). Mandrel (230) can be any shape that is suitable to allow sleeve ring (435) to be coupled to mandrel (230), retained by mandrel (230), and/or released from mandrel (230).

One or more rollers (220) are configured to contact sleeve (330) and while rotating, force sleeve (330) proximally over sleeve ring (435). In certain embodiments, one or more rollers (220) press sleeve (330) against sleeve ring (435) to ensure grip is maintained between one or more rollers (220) and sleeve (330). The contact surface of one or more rollers (220) may be made from polyurethane or any other similar material which will increase the friction between one or more rollers (220) and sleeve (330). Increasing the friction between one or more rollers (220) and sleeve (330) improves the consistency the sleeve (435) will fold evenly round the perimeter of sleeve ring (435) without bunching or tearing.

In the example shown, folding device (200) includes four rollers (220) to fold sleeve (330) on sleeve ring (435). Increasing the number of rollers (220) subsequently increases the contact area with the one or more rollers (220) with sleeve (330), and therefore improve the consistency of the folding. In other embodiments, one or more rollers (220) may be self-righting or floating in order to maximize the contact with sleeve (330) by maintaining proper pressure and positioned of one or more rollers (20). In such embodiments, the term self-righting can refer to, for example, the ability for the rollers (220) to be generally pivotable about an axis, while also being biased towards a given position. Accordingly, such self-righting rollers (220) can be configured to permit some flexion during rolling, but still rotate around the same general axis of rotation. One or more rollers (220) may also be configured to automatically or manually move away from or toward mandrel (230) to allow for loading or removal of sleeve ring (435). In the current example, one or more rollers (220) are substantially cylindrical, however one or more rollers can be any shape or size that is suitable for the device (200) as would be well known by those having skill in the art.

Figure 5:
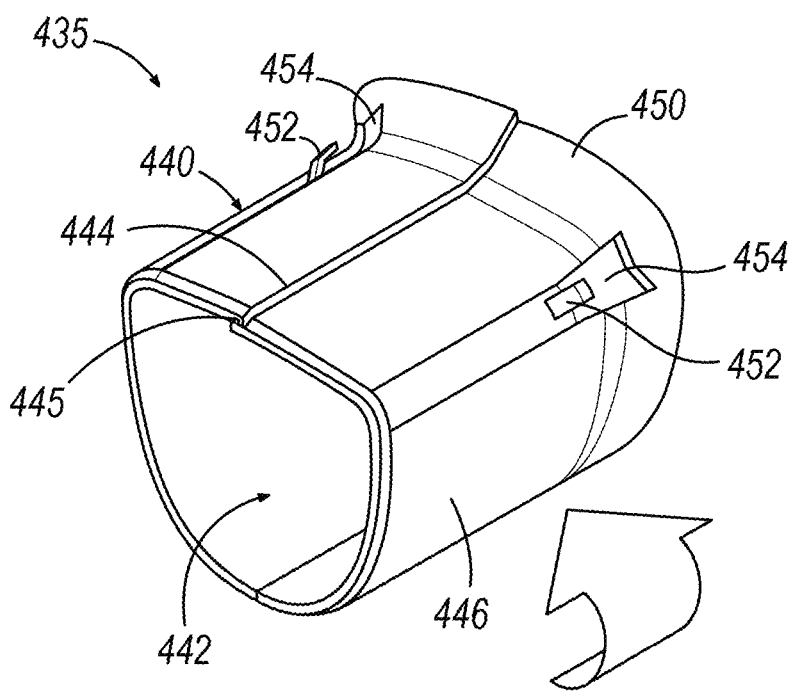
FIG. 5 depicts a perspective view of an exemplary sleeve ring of the sleeve assembly of FIG. 4, the sleeve ring in a flexed configuration.

FIG. 5 shows an exemplary sleeve ring (435) or short rigid retainer that may be readily used with sleeve (330). Sleeve ring (435) is generally configured fasten to sleeve (330) to enhance the manipulation of sleeve (330). As will be understood, sleeve (330) is generally configured as a thin elastomeric sterile cover for use with an instrument such as a biopsy device. Sleeve (330) may therefore have a relatively long length to promote sterility of the instrument and other parts associated with the instrument. As such, it may be desirable to use sleeve (330) in connection with sleeve ring (435) to promote ease of use—particularly when attaching sleeve (330) to the instrument. Although sleeve (330) is referred to herein simply as "sleeve," it should be understood that in other contexts other terms may be used such as elastomer thin sleeve, flexible sterile cover, sterile cover, and/or etc.

Sleeve ring (435) includes a body (440) that defines a sheath portion (446) and a horn portion (450). As will be described in greater detail below, body (440) is generally configured to receive inner retainer (310) or other components that may be associated with a device such as a biopsy device. Body (440) is shown as defining a hollow interior (442) that forms a d-shape that generally corresponds to the shape of inner retainer (310). Although body (440) is shown and described herein as having a particular shape, it should be understood that in other examples, the shape of body (440) can be modified to any other suitable shape corresponding to the shape of inner retainer (310).

Body (440) defines a relief slot (444) extending longitudinally along the length of body (440). Body (440) generally comprises a thin relatively flexible material such as a plastic or polymer. Thus, body (440) has at least some flexibility. To further enhance this flexibility, relieve slot (444) is generally configured to permit a portion of body (440) to fold over onto itself to thereby reduce the size of body (440). As will be described in greater detail below, this configuration is generally desirable to promote attachment of sleeve (330) to sleeve ring (435).

Relief slot (444) includes an interlocking portion (445) defined by body (440) on either side of relief slot (444). As will be described in greater detail below, interlocking portion (445) is generally configured to provide some rigidity to body (440) when body (440) is compressed to close relieve slot (444). In the present example, interlocking portion (445) includes a tongue and groove configuration comprising a triangular tongue and corresponding triangular groove. In other examples, other suitable interlocking features can be used such as a square tongue and a square groove, a rounded tongue and a rounded groove, and/or etc.

Sheath portion (446) defines a substantial portion of the longitudinal length of body (440). Sheath portion (446) is generally configured to hold a portion of sleeve (330) in a compressed or folded configuration. As will be described in greater detail below, this feature may be desirable to manage excess portions of sleeve (330) when sleeve (330) is not in use. Sheath portion (446) can define a variety of suitable lengths. For instance, suitable lengths of sheath portion (446) will be apparent to those of ordinary skill in the art in view of the teachings herein.

Horn portion (450) extends proximally and outwardly relative to sheath portion (446). As can be seen, horn portion (450) provides a generally frustoconical shape. In other words, horn portion (450) is generally flared outwardly relative to sheath portion (446). This configuration provides an enlargement of hollow interior (442) of body (440) to thereby enhance access to hollow interior (442). As will be described in greater detail below, enhanced access may be desirable to aid in inserting components such as inner retainer (310) into sleeve ring (435) and into sleeve (330). Additionally, the flared nature of horn portion (450) provides enhanced gripping of sleeve ring (435) to thereby enhance manipulation of sleeve (330).

Sleeve ring (435) further includes a plurality of tabs (452, 458) extending proximally and outwardly from body (440) near the interface between sheath portion (446) and horn portion (450). Tabs (452, 458) are generally configured to grip at least a portion of sleeve (330) to provide releasable attachment between sleeve ring (435) and sleeve (330). As will be described in greater detail below, sleeve (330) generally extends distally from sleeve ring (435) when attached thereto. Thus, tabs (452, 458) extend in a proximal direction relative to body (440) while also extending outwardly. This configuration permits a portion of sleeve (330) to fold over and underneath tabs (452, 458) to releasably hold sleeve (330) in position.

In the present example, tabs (452, 458) include a pair of upper tabs (452) and a single lower tab (458). Upper tabs (452) are positioned at the upper inflexion points in the shape of body (440). Meanwhile lower tab (458) is positioned at the lower inflexion point in the shape of body (440). Although upper tabs (452) and lower tab (458) are described separately herein, it should be understood that upper tabs (452) and lower tab (458) are generally substantially similar to each other except as where otherwise noted herein.

Beneath each tab (452, 458), body (440) defines an opening (454, 460) associated with each tab (452, 458). Openings (454, 560) are generally configured to provide additional clearance that permits sleeve (330) to fully engage each tab (452, 458). For instance, in the absence of openings (454, 460), the curvature of horn portion (450) could potentially interfere with engagement between sleeve (330) and tabs (452, 458) by sleeve (330) riding up the curvature of horn portion (450).

Openings (454, 460) include a pair of upper openings (454) and a single lower opening (460). Upper openings (454) are associated with upper tabs (452). Meanwhile, lower opening (460) is associated with lower tab (458). Each upper opening (454) is enclosed on all four sides of the rectangular shape defined by each upper opening (454). This configuration is generally due to the curvature of horn portion (450) in the area associated with upper openings (454). In particular, since the curvature of horn portion (450) is relatively steep in the area associated with upper openings (454), it is desirable to entirely enclose upper openings (454). Meanwhile, the proximal face of lower opening (460) is open due to the relatively low slope of the curvature of horn portion (450) in the area associated with lower opening (460).

As seen in FIG. 5, sleeve ring (435) can be initially manipulated to flex body (440) to collapse on itself via relief slot (444). This causes one of the edges that defines relief slot (444) to fold under another edge. As a consequence, the overall size of sleeve ring (435) is reduced. This reduction in size can make it easier for an operator to stretch sleeve (330) over sheath portion (446) of body (440). Although FIG. 5 only shows a relatively small amount of flexion, it should be understood that sleeve ring (435) can be flexed any suitable amount depending on a variety of factors such as the elasticity of sleeve (330), the size and/or shape of sleeve (330), the relative strength of the operator, and/or etc. For instance, in some examples, sleeve ring (435) can be flexed until an edge defining relief slot (444) touches the opposite inflexion point or corner formed by body (440). Thus, the width of sleeve ring (435) can be reduced approximately in half in some uses. Of course, various alternative amounts of flexion can be used as will be apparent to those of ordinary skill in the art in view of the teachings herein.

In certain embodiments sleeve ring (435) can be expanded when coupled with mandrel (230), or the sleeve ring (435) may be expanded after removal from mandrel (230). Mandrel (230) may include a wedge that will advance and automatically spread sleeve ring (435) to an expanded state. Additionally, in some embodiments sleeve ring (435) may not collapse and retain its shape as a solid rigid piece. Sleeve ring (435) may also be configured to maintain a form to enhance the ability to hold and retain sleeve (330). In some embodiments, sleeve ring (435) may include a windows or slots so that an idle roller (not shown) may pass through and press against each of one or more rollers (220) through sleeve (330) in order to reduce friction and allow sleeve (330) to fold more freely.

II. EXEMPLARY SLEEVE FOLDING TRANSMISSION ASSEMBLY

Figure 6A:
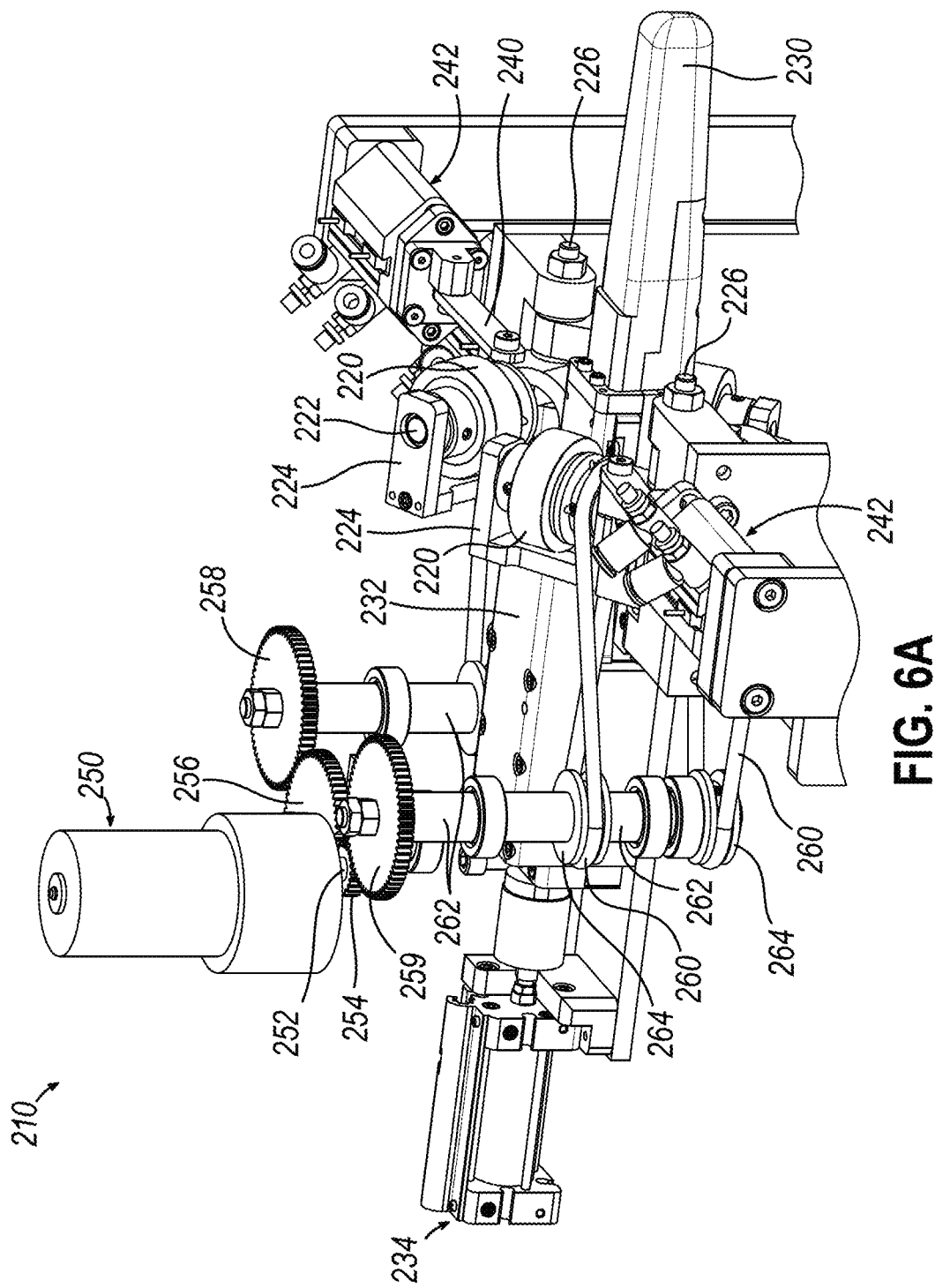
FIG. 6A depicts a perspective detail of view of a transmission assembly of the sleeve folding device of FIG. 1.
Figure 6B:
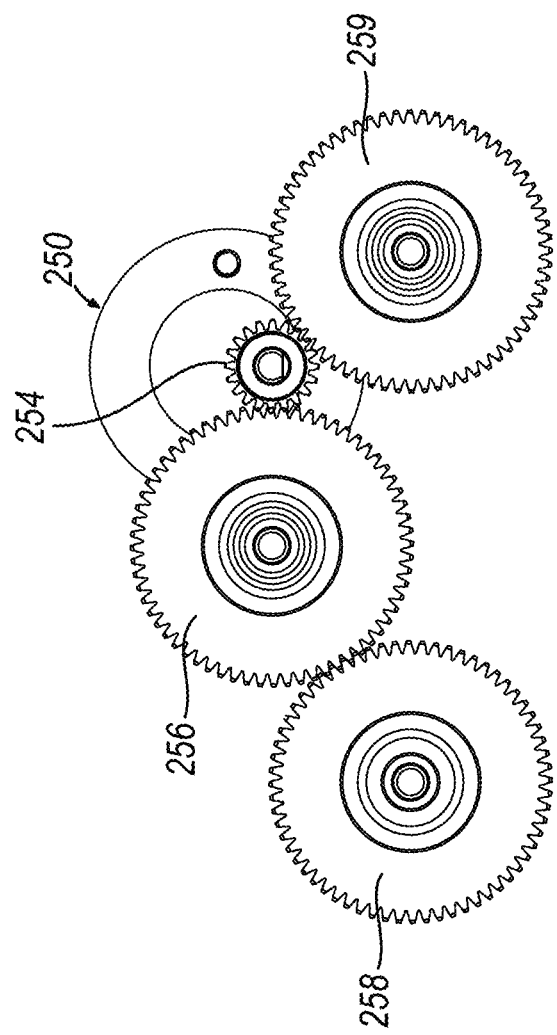
FIG. 6B depicts a bottom plan view of the transmission assembly of FIG. 6.
Figure 7:
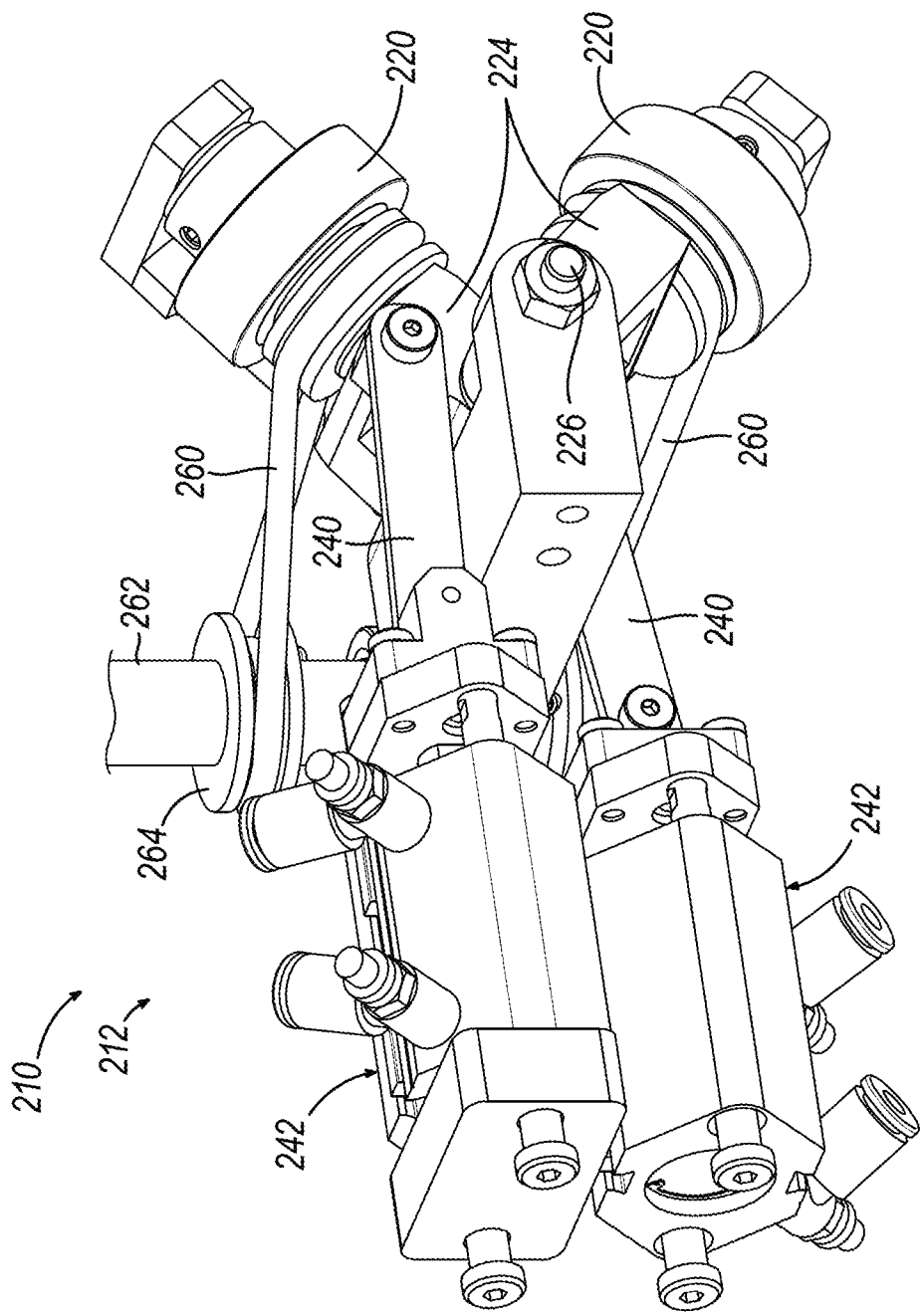
FIG. 7 depicts a detailed perspective view of a roller assembly of the sleeve folding device of FIG. 1.

Referring now to FIGS. 6A, 6B, and 7, transmission assembly (210) is configured to drive both the translation of mandrel (230) and the rotation of one or more rollers (220), as well as pivoting or translation of one or more rollers (220) toward and away from mandrel (230). Transmission assembly (210) is shown and described herein as including certain specific drive means, it should be understood that in other examples, transmission assembly (210) can include a variety of alternative or additional drive means. Additionally, it should be understood that in some examples, transmission assembly (210) may include two transmission systems for driving one or more rollers (220) and mandrel (230) separately. As will be understood, transmission assembly (210) is configured to provide coordinated linear motion of mandrel (230) with the rotation of one or more rollers (220). In some examples, this coordination can be based on the rotation of rollers (220). By way of example only, by tracking the rotation of rollers (220), such tracking can be used to maintain a constant proportion of revolutions of one or more rollers (220) and the linear motion of mandrel (230). Generally, the linear motion of mandrel (230) is proximal or rearward as one or more rollers (220) are folding sleeve (330) onto sleeve ring (435). In the present example, transmission assembly (210) is configured to move mandrel (230) distally or forward after sleeve has been folded on sleeve ring (435).

In some examples, the speed of the rotation of one or more rollers (220) and the corresponding speed of mandrel (230) due to the required ratio is preprogrammed by a computer coupled to the transmission assembly (210). In other examples, the speed of the rotation of one or more rollers (220) and the corresponding speed of mandrel (230) is set by gearing or other mechanical means. The speed of the rotation of each of one or more rollers (220) and the corresponding speed of mandrel (230) may be variable with one or more rollers (220) as sleeve (330) is rolled onto sleeve ring (435) in order to fold sleeve (330) more consistently and prevent one portion of sleeve (330) from folding less or more than another portion. In certain embodiments, transmission assembly (210) may include direct drive to each of one or more rollers (220). In other embodiments, each of one or more rollers (220) are independently driven to allow for more precision in the folding of sleeve (330) so that speed, torque, pressure, or other parameters can be altered independently of other rollers (220). Independently driven rollers (220) can additionally prevent or minimize slippage of one or more rollers (220) and prevent self-locking of sleeve (330) as it is folded when one roller (330) advances a portion of sleeve (330) further than another portion, causing sleeve (330) to advance unevenly and stop advancing at all. Preventing or avoiding self-locking may be achieved by speeding up or slowing down individual rollers (220) when self-locking is anticipated or is occurring. The monitoring fore self-locking behavior of the sleeve (330) can be done by visual systems or any other suitable monitoring systems. Transmission system (100) may be powered by electrical power (electrical cables), rotary power (rotary drive cable), and/or pneumatic power (pneumatic cables).

As shown in FIGS. 6A and 6B, transmission assembly (210) of the present example comprises a rotational motor (250) configured to drive rotation of each roller (220). In particular, rotational motor (250) is in communication with a series of gears (254, 256, 258, 259), which communicate rotary motion from motor (250) to two rotational shafts (262). As will be described in greater detail below, each rotational shaft (262) is in communication with two of the four rollers (220) via a connection tube (260) for each roller (220) to generally transfer rotary motion from motor (250) to rollers (220). As will be understood, this configuration results in a fixed coordinated rotation of rollers (220) though a mechanical arrangement. However, it should be understood that in other examples, such coordinated rotation of rollers (220) can be provided through other arrangements such as electronic coordination.

FIG. 6B shows an exemplary layout of the gears (254) that are used to transfer rotary motion from rotational motor (250) to rotational shafts (262). As can be seen, drive gear (254) is in communication with rotational motor (250) by drive shaft (252) such that rotational motor (250) is configured to drive rotation of drive gear (254). Drive gear (254) is in turn in communication with both a first shaft gear (259) and a coupling gear (256). First shaft gear (258) is in communication with one of two rotational shafts (262). Meanwhile, coupling gear (256) is in communication with a second shaft gear (258), which is in communication with another one of two rotational shafts (262).

In the present example, coupling gear (256) is used merely to change the direction of rotation for second shaft gear (258) without effecting the gear ratio of second shaft gear (258) relative to drive gear (254). Thus, it should be understood that gears (254, 256, 258, 259) are arranged in the present example to drive rotation of each of the two rotational shafts (262) at the same speed of rotation. As a result, it should be understood that all four rollers (220) are driven at the same rotational speeds. Meanwhile, it should also be understood that gears (254, 256, 258, 259) are arranged in the present example to drive rotation of one rotational shaft (262) in an opposite direction relative to another rotation shaft (262). This opposite rotation results in each roller (220) on a given side of mandrel (230) applying a linear folding force to the mandrel (230) in the same direction as a corresponding linear folding force applied by rollers (220) oriented on an opposite side of mandrel (230). Thus, the opposite rotation is generally configured to permit rollers (220) to fold sleeve (330) in the same linear direction.

As best seen in FIGS. 6A and 7, each rotational shaft (262) comprises one or more transfer seats (264). In the present examples, each rotational shaft (258) comprises two transfer seats (264), with each transfer seat corresponding to a single roller (220). In the present example, each transfer seat (264) is configured to receive a portion of a connection tube (260), which is used to communicate rotary motion from a respective rotational shaft (258) to a corresponding roller (220). Although not shown, it should be understood that transfer seats (264) can include certain geometric features to aid in receiving connection tube (260). For instance, in some examples each transfer seat (264) can have a semi-circular indentation extending around the generally cylindrical shape of each transfer seat (264). In addition, in such examples such an indentation can include rough sections, dimples, protrusions, knurling, or other surface finishes to promote grip between each transfer seat (264) and a corresponding connection tube (260).

Connection tubes (260) are flexible tubes or pipes configured to rotate as rotational shafts (262) rotate and cause rollers (220) to rotate. Connection tubes (260) can comprise a variety of materials. For instance, in some examples, connection tubes (260) comprise a flexible polymer or rubber material. In such examples, connection tubes (260) can exhibit some axial elastomeric properties. Alternatively, in other examples, connection tubes (260) can be relatively stiff or otherwise resistant to stretching. In the present example, connection tubes (260) are generally desirable to transfer rotary motion to rollers (220), while also providing some degree of movement in rollers (220) with minimal impact on rotation. In alternative embodiments, other arrangements of the shafts are contemplated as would be obvious to one skilled in the art. In alternative embodiments, other arrangements of the gearing, shafts, and tubing are contemplated as would be obvious to one skilled in the art.

As shown in FIG. 7. transmission assembly (210) also includes one or more roller assemblies (212). In the present example, transmission assembly (210) includes two roller assemblies (212) oriented on either side of mandrel (230). As will be understood, each roller assembly (212) supports two rollers (220). This configuration is generally desirable to promote ease of assembly, while also providing for manipulation of rollers (220). As can be seen, each roller assembly (212) includes the following for each roller (220)—a translating drive motor or actuator (242), a translating drive rod (240), a fixed roller shaft (226), and a roller arm (224). Translating drive motor (242) is coupled to translating drive rod (240) and is configured to move translating drive rod (240) in linearly. In the present example, translating drive motor (242) is a pneumatic actuator, although any other suitable actuator can be used such as a solenoid, rack and pinion actuator, geared motor, and/or ect.

Translating drive rod (240) extends from translating drive motor (242) to roller arm (224) and is configured to translate toward and away from mandrel (230) in coordination with translating drive motor (242). Translating drive rod (240) is further pivotably coupled to roller arm (224) by a screw, pin, fastener, or other coupling means. Although not show, it should be understood that translating drive rod (240) can also be pivotably coupled to translating drive motor (242). Thus, it should be understood that translating drive rid (240) is generally configured as a mechanical link between translating drive motor (242) and roller arm (224) to pivot a corresponding roller (220) towards and away from mandrel (230).

Roller arm (224) is generally configured to pivot about fixed roller shaft (226). On an end of roller arm (224) opposite of fixed roller shaft (226), a roller (220) is rotatably mounted. Translating drive rod (240) can generally be fastened at any point on roller arm (224) between fixed roller shaft (226) and roller (220). However, in the present example, translating drive rod (240) is generally fastened proximate roller (220) to provide increased mechanical advantage in comparison to fastening positions proximate to fixed roller shaft (226). Regardless, it should be understood that translating drive rod (240) is generally configured to translate forward or rearward to thereby pivot roller arm (224) about fixed roller shaft (226) to move roller (220) moves toward or away from mandrel (230) as described above.

Roller shaft (226) in the present example is configured to accommodate two roller arms (224). In this configuration, one roller arm (224) can be forked, while another can be solid to permit both roller arms (224) to pivot along the same plane while being mounted to a single roller shaft (226). This configuration is generally desirable to reduce the amount of material needed in manufacturing and to make roller assembly (212) more compact. However, it should be understood that in other examples multiple roller shafts (226) can be used, with each roller shaft (226) corresponding to a single roller arm (224).

Figure 8:
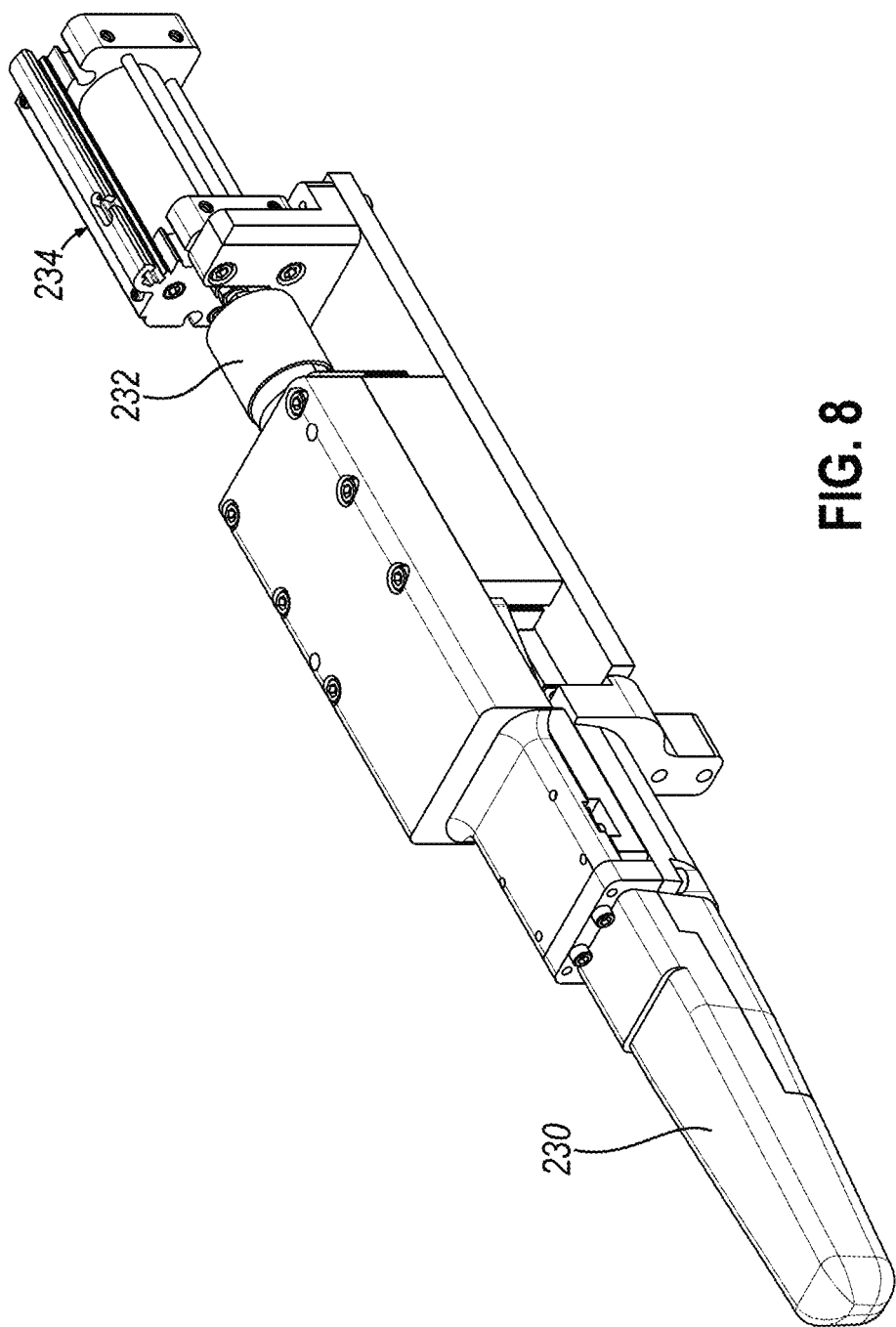
FIG. 8 depicts a perspective view of a mandrel of the sleeve folding device of FIG. 1.

As best seen in FIG. 8, mandrel (230) is generally configured to for translation via mandrel actuator (234). In particular, a proximal or rear end of mandrel (230) is fixedly secured to a pushrod (232) extending between mandrel actuator (234) and mandrel (230). Thus, pushrod (232) transfers linear motion of mandrel actuator (234) to mandrel (230). Mandrel actuator (234) in the present example is a pneumatic actuator. However, it should be understood that in other examples, mandrel actuator (234) can take on a variety of forms such as a solenoid, a rack and pinion mechanism, a leadscrew based linear actuator, or any other suitable actuator.

Although not shown, it should be understood that in the present example, rotational motor (250), translating drive motor (242), and mandrel actuator (234) can all be in communication with one or more controllers or control modules to coordinate motion of rollers (220) with motion mandrel (230). In some examples, such controllers can also be in communication with sensors, encoders, and/or other devices to form a control system configured further facilitate coordination of motion. For instance, in some examples, rollers (220) can be in communication with one or more encoders to communicate data related to rotation of rollers (220) to a controller. Similarly, mandrel (230) can be in communication with a linear encoder or other sensor to likewise communication data related to translation of mandrel (230) to a controller. One or more controllers can then process such data and control operation of one or more of rotational motor (250), translating drive motor (242), and/or mandrel actuator (234) to coordinate movement of rollers (220) with movement of mandrel (230). While various mechanical and electromechanical mechanisms for coordinating motion are described herein, it should be understood that other forms of coordinating motion may be used as will be apparent to those of ordinary skill in the art in view of the teachings herein.

As described above, rotation of rollers (220) is generally coordinated with translation of mandrel (230). This coordination can be controlled by the control system described above. In some examples, the control system can be configured to rotate rollers (220) in a fixed or dynamic ratio relative to translation of mandrel (230). For instance, in some examples this ratio can be characterized by a ratio of rotations per minute to a linear unit of measure per minute. In other examples, the ratio can be based on the circumference of each roller per unit of time rather than a number of rotations per unit of time. In such examples, the ratio may be fixed to some amount greater than 1/1 because otherwise rollers (220) and mandrel (230) would move at the same rate and no folding of sleeve (330) would result. It should be understood that various suitable ratios will be apparent to those of ordinary skill in the art in view of the teachings herein.

III. EXEMPLARY METHOD OF SLEEVE FOLDING

Figure 9A:
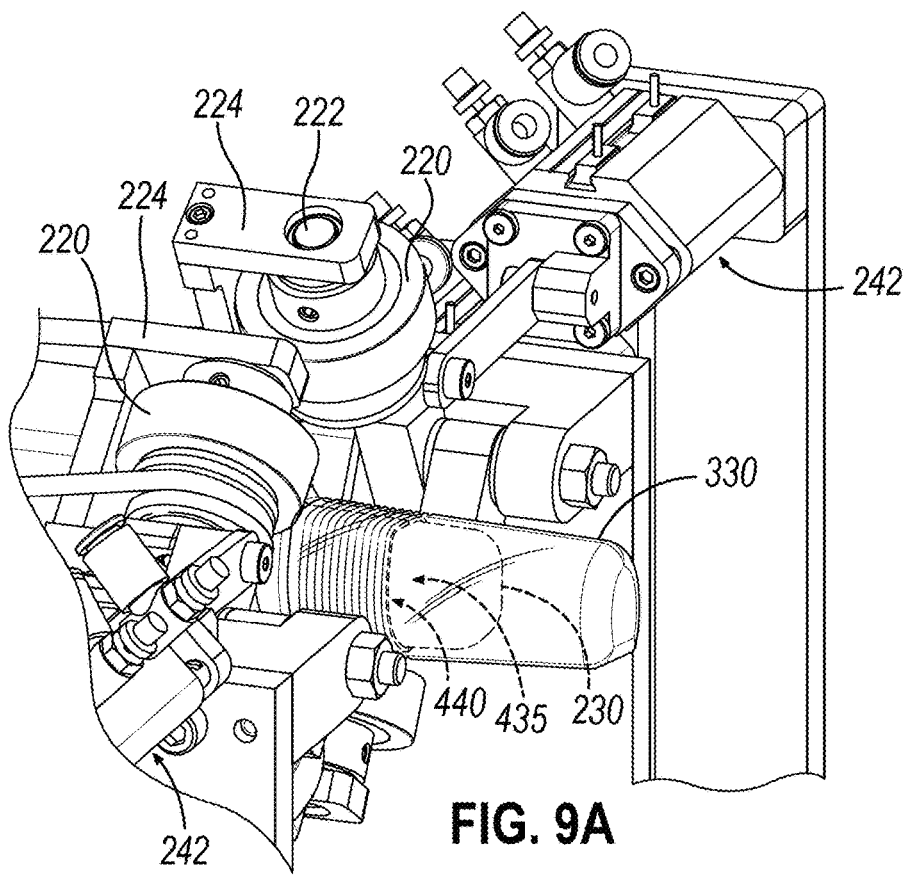
FIG. 9A depicts a perspective view of the alternative sleeve assembly of FIG. 4 coupled to the sleeve folding device of FIG. 1, the sleeve folding device in a retracted position.

FIGS. 9A through 9F show the process of folding elastomer thin sleeve (330) on sleeve ring (435) using folding device (200). The embodiment shown is only one of any number of variations that would be obvious to one skilled in the art. It should be understood that minor variations in the process not discussed below are well known to those having skill in the art. As shown in FIG. 9A, mandrel (230) can be initially in a partially retracted position. At this stage, sleeve (330) can be partially folded on to sleeve ring (435) and placed on mandrel (230).

Once sleeve (330) is placed onto mandrel (230), the folding process can begin. To accomplish folding, rollers (220) are pivoted into position against sleeve (330) and mandrel (230) via translating drive motor (242). Once in place, rollers (220) are rotated using rotational motor (250). As rollers (220) rotate, sleeve (330) is folded onto sleeve ring (435). Simultaneously, mandrel (230) can be retracted to prevent bunching or self-locking of sleeve (330).

Figure 9B:
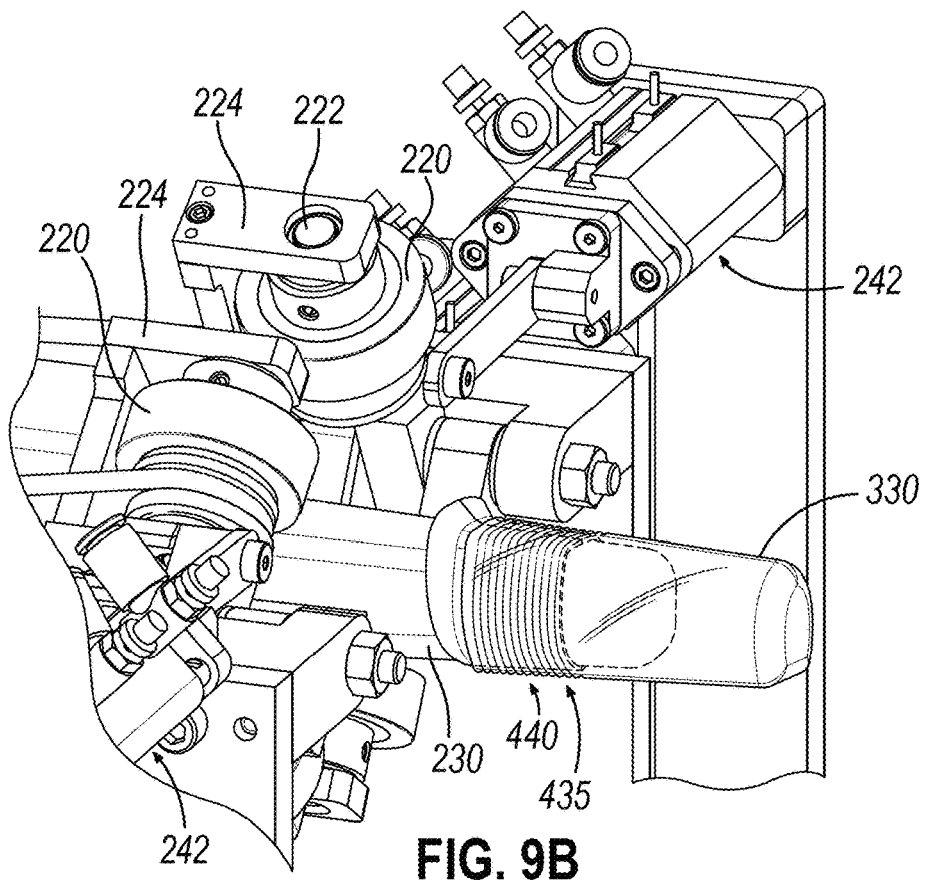
FIG. 9B depicts a perspective view of the alternative sleeve assembly of FIG. 4 coupled to the sleeve folding device of FIG. 1, the sleeve folding device in a protracted position.

As shown in FIG. 9B, mandrel (230) of device (200) is in a protracted position. In some uses, mandrel (230) can be automatically transitioned to the protected position after folding of sleeve (330) onto sleeve ring (435) is complete. In addition, or in the alternative, sleeve (330) can also be loaded onto mandrel (230) while mandrel (230) is in the protected position.

Figure 9C:
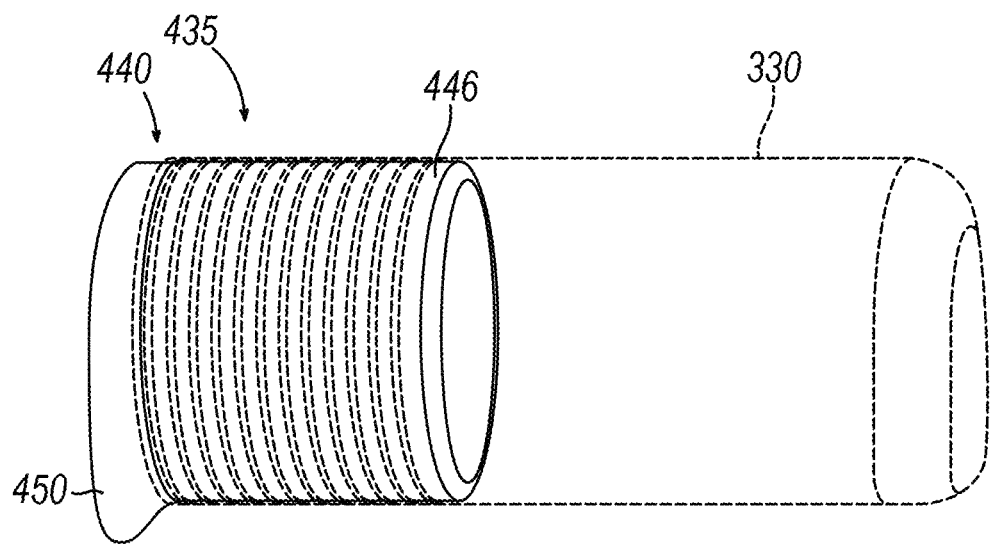
FIG. 9C depicts a side elevational detail view of the exemplary sleeve assembly of FIG. 4, the exemplary sleeve assembly in a partially compressed state.

As shown in FIG. 9C, sleeve (330) is substantially folded on the sheath portion (446) of body (440) of sleeve ring (435) after the folding procedure described above. Once sleeve (330) is folded onto sleeve ring (435), the proximal end of sleeve (330) is positioned near the proximal end of sleeve ring (435), abutting horn portion (450). Additionally, folding can be performed such that a portion of sleeve (330) remains loose or otherwise unfolded relative to sleeve ring (435). Such a loose portion (450) can be desirable in some uses to facilitate insertion of one or more devices into sleeve (330), as will be described in greater detail below.

Figure 9D:
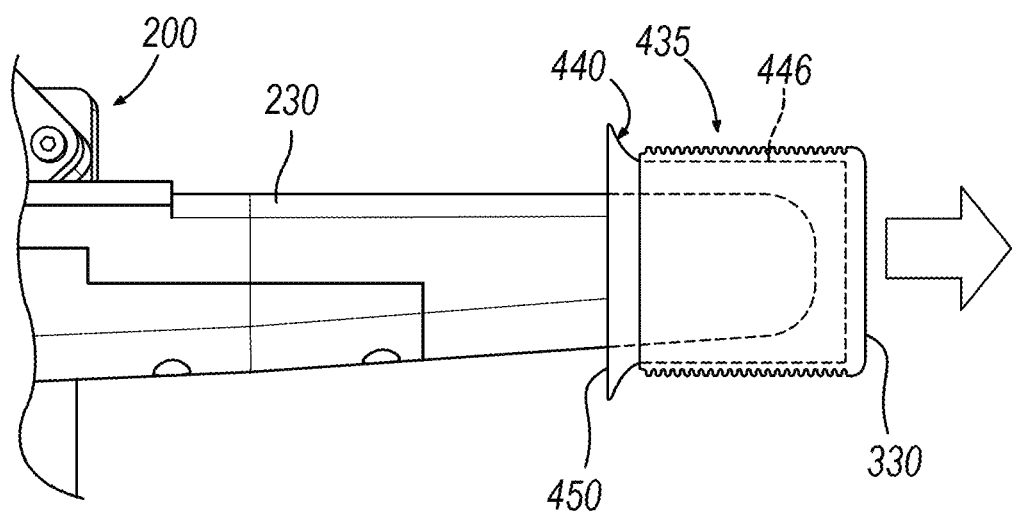
FIG. 9D depicts a side cross-sectional view of the exemplary sleeve assembly of FIG. 4 coupled with the sleeve folding device of FIG. 1, the exemplary sleeve assembly in an extended, ejected state.

FIG. 9D show the ejection of sleeve ring (435) from mandrel (230) in greater detail. As described above, this operation can occur when mandrel (230) is in the protracted position. Alternatively, in some uses, this operation can occur when mandrel (230) is in the retracted position. In either case, sleeve (330) and sleeve ring (435) can be together ejected or otherwise removed from mandrel by hand. In some uses, hand-based removal may be desirable to reduce the susceptibility of tearing of sleeve (330). In other uses, removal can be performed automatically by an ejector or other mechanical mechanism. In such automatic removal may be desirable in some uses to promote sterility of sleeve (330) and/or sleeve ring (435).

Figure 9E:
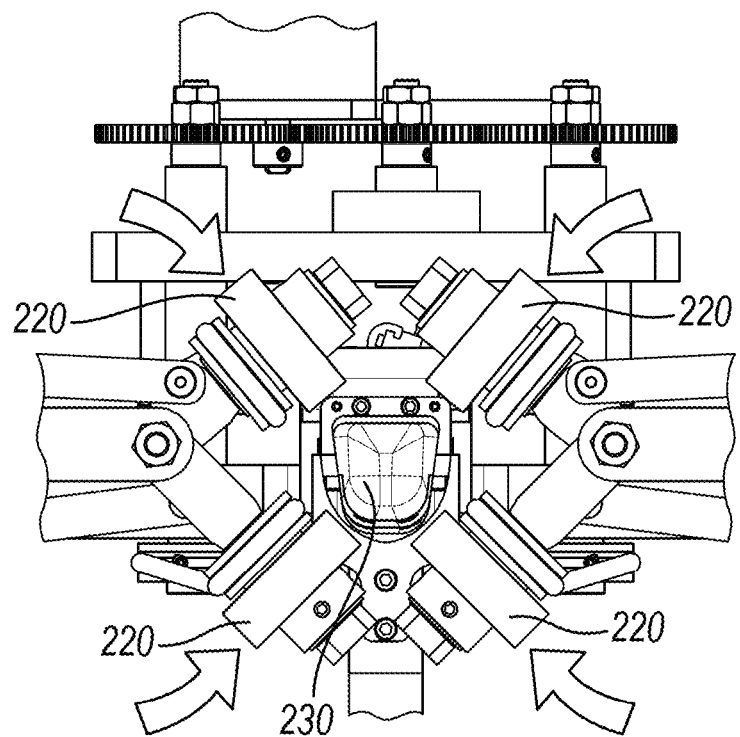
FIG. 9E depicts a front elevational view of the roller in a closed position of the sleeve folding device of FIG. 1.
Figure 9F:
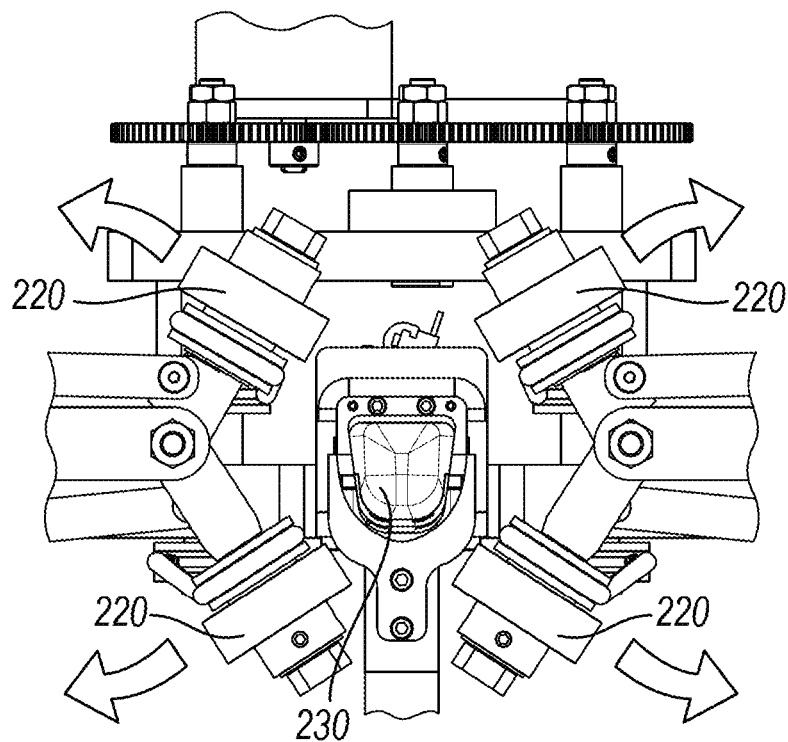
FIG. 9F depicts a front elevational view of the roller in an open position of the sleeve folding device of FIG. 1.

As described above, rollers (220) in the present example are generally configured to selectively move away from or toward mandrel (230) to allow for loading or removal of sleeve ring (435). FIGS. 9E and 9F show such movement of each roller (220). For instance, in FIG. 9E, rollers (220) are pivoted inwardly towards mandrel (230) from an open position to a closed position. In some uses, this movement can be used after loading of sleeve (330) and sleeve ring (435) onto mandrel (230). In particular, rollers (220) in the open position can provide enhanced access to mandrel (230), thereby promoting ease of loading. Similarly, rollers (220) in the closed position can contact sleeve (330) for folding purposes.

FIG. 9F shows each roller (220) moving from the closed position to the open position. In use, this movement can be used after the folding operation described above is completed. For instance, once folding is completed, rollers (220) can be moved to the open position as shown in FIG. 9F for removal of sleeve (330) and sleeve ring (435). In this position, rollers (220) provide sufficient clearance between rollers (220) and mandrel (230) for removal of sleeve (330) and sleeve ring (435).

Although not shown, it should be understood that in some examples, one or more rollers (220) can be configured to move independently of each other, or one or more rollers (220) may move toward or away from mandrel (230) rather than in the synchronized manner shown in FIGS. 9E and 9F. Such independent motion of rollers (220) may be desirable in some uses to promote flexibility during operation.

Figure 10:
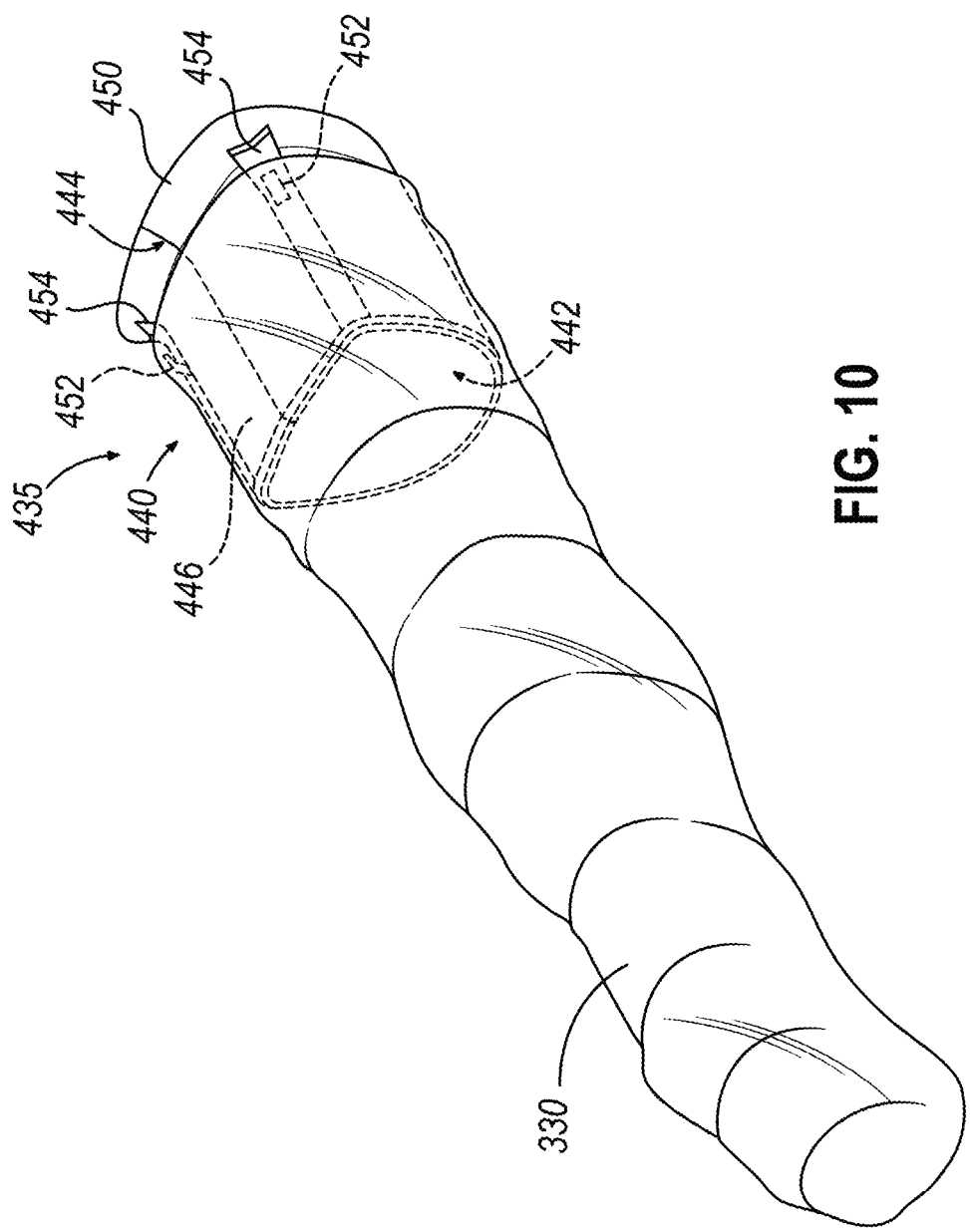
FIG. 10 depicts a perspective view of the alternative sleeve assembly of FIG. 4, the sleeve assembly in an extended state.
Figure 11:
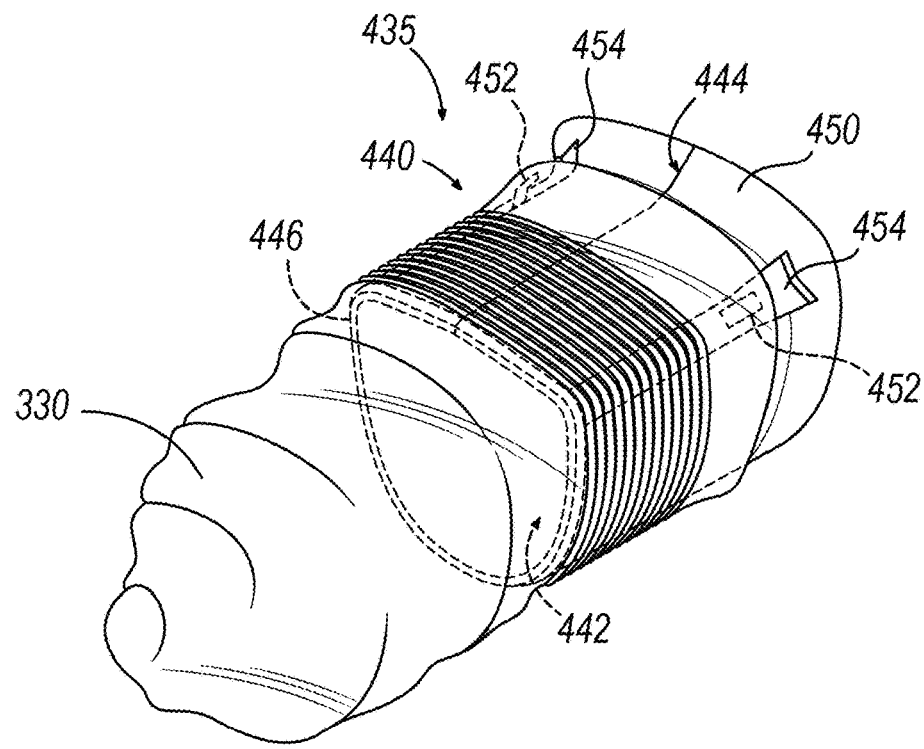
FIG. 11 depicts a perspective view of the alternative sleeve assembly of FIG. 4, the sleeve assembly in a compressed state.

FIGS. 10 and 11 show sleeve (330) and sleeve ring (435) in an initial non-folded configuration and a folded configuration, respectively. The initial non-folded configuration generally corresponds to the use described above with respect to FIG. 9A and loading of sleeve (330) onto mandrel (230). Similarly, the folded configuration generally corresponds to the use described above with respect to FIG. 9B and unloading of sleeve (330) from mandrel (230) after completion of the folding procedure.

As also shown in FIG. 11, once sleeve (330) is secured to sleeve ring (435), body (440) can be decompressed to open relief slot (444). Once relief slot (444) is open, the resiliency of sleeve (330) causes relief slot (444) to close on itself, thereby engaging interlocking portion (445). In the present example, the triangular tongue of interlocking portion (445) engages the triangular groove of interlocking portion (445) to provide additional structural rigidity to body (440). Although this decompression step is shown as occurring after sleeve (330) is initially attached to sleeve ring (435), it should be understood that this step can be instead performed later in the procedure, as will be described in greater detail below.

As described above, the folded configuration of sleeve (330) on sleeve ring (435) is generally facilitated by rollers (220) along with movement of mandrel (230). Although this operation is described above using the term "folding," it should be understood that this operation can be characterized in a variety of other ways. For instance, in some characterizations, sleeve (330) is rolled or compressed onto the sleeve ring (435) in a zig-zag accordion-like manner. Regardless of the particular characterization, once sleeve (330) positioned onto sleeve ring (435), sheath portion (446) is generally used to store any excess length of sleeve (330) until use of sleeve (330) is desired. As described above, this feature may be desirable in certain contexts to make the assembly of sleeve (330) and sleeve ring (435) easier to manipulate before the entire length of sleeve (330) is needed.

Figure 12:
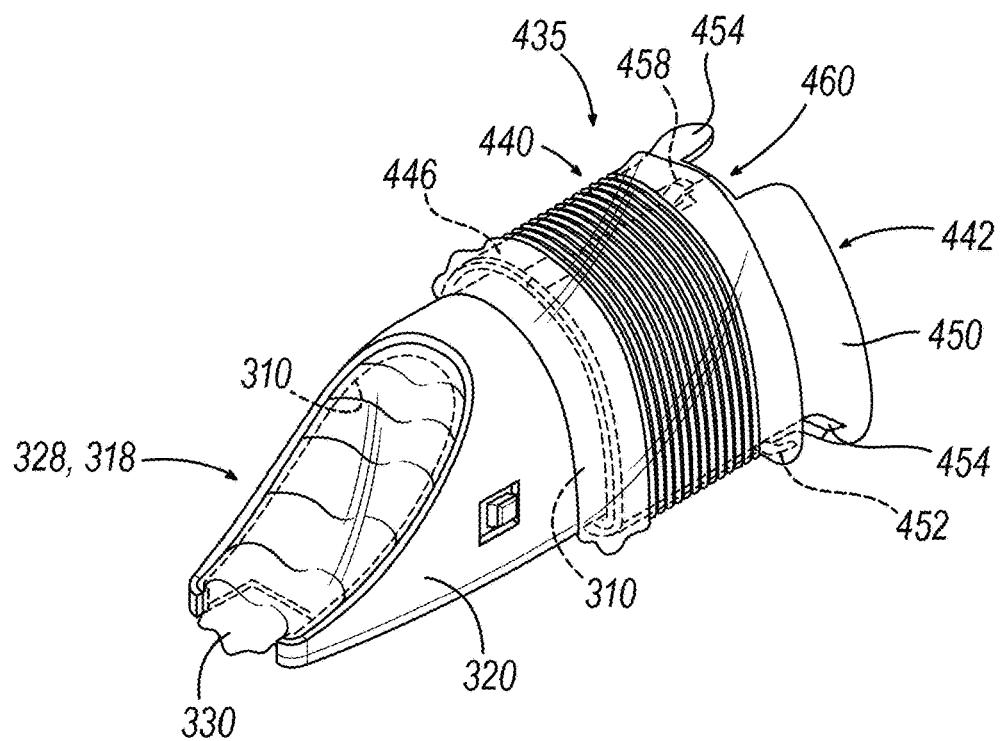
FIG. 12 depicts a perspective view of the alternative sleeve assembly of FIG. 4 coupled with inner and outer retainers.

As shown in FIG. 12, an operator can next insert inner retainer (310) into sleeve (330) via hollow interior (442) of sleeve ring (435). Although this step can be performed regardless of whether sleeve (330) is in the un-folded position (FIG. 10) or folded position (FIG. 11), the folded position is generally more desirable because inner retainer (310) will not have to travel as far through sleeve (330) before reaching the distal end of sleeve (330).

FIG. 12 generally shows the combination of sleeve ring (435), inner retainer (310), outer retainer (320), and sleeve (330) for use with a device such as a biopsy device. In this configuration, inner retainer (310) is inserted into sleeve (330). With inner retainer (310) inserted therein, external sleeve (320) can be secured to inner retainer (310) with sleeve (330) disposed between inner retainer (310) and outer retainer (320). Sleeve ring (435) can then be used to manipulate the proximal end of sleeve (330). This configuration may be desirable to permit attachment of inner retainer (310) to one or more components of a device such as a holster of a biopsy device. To that end, it should be understood that at various points during assembly of sleeve ring (435), inner retainer (310), outer retainer (320), and sleeve (330), an operator may create slits, openings, ports and/or etc. in sleeve (330) to permit communication between the holster and other portions of the biopsy device. By way of example only, such slits, openings, ports, and/or etc. may be created by using a sharp tool such as a razor to cut, slice, or perforate sleeve (330). Sleeve ring (435) can then be used to unfurl sleeve (330) to cover one or more components of the device. The particular length of sleeve (330) can generally be sized to provide approximately 2.5 feet of coverage, although this length may be varied in other examples.

It should be understood that the state shown in FIG. 12 corresponds to the assembly being in a shipped or packaged state. In other words, when an operator first removes the combination of sleeve ring (435), inner retainer (310), outer retainer (320), and sleeve (330) from sterile packaging, the combination can be in the state shown in FIG. 12. As can be seen, in the packaged state, inner retainer (310) is nested within outer retainer (320). Sleeve (330) is positioned between inner retainer (310) and outer retainer (320). As can be seen, sleeve (330) is visible through top sleeve openings (318, 328). At least a portion of sleeve (330) is covered by outer retainer (320) before emerging from proximal sleeve opening (324). At this point, at least a portion of sleeve (330) can be folded distally over outer retainer (320). Sleeve (330) then passes proximally over inner retainer (310) until reaching sleeve ring (435). At sleeve ring (435), sleeve (330) is compressed, rolled, folded, or bunched over sheath portion (446), as described above.

Once an operator places a device within the combination of sleeve ring (435), inner retainer (310), outer retainer (320), and sleeve (330), the operator can pull sleeve ring (435) proximally away device. This can cause sleeve (330) to unroll, decompress, or otherwise extend in length as sleeve (330) is pulled off of sheath portion (446).

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A folding device for placing an elastomer thin sleeve on a retainer, the folding device including a mandrel configured to translate relative to a portion of the folding device, wherein the mandrel is adapted to releasably receive the retainer; one or more rollers configured to rotate relative to the mandrel, wherein the rotation of the one or more rollers is configured to fold the sleeve onto the retainer; and a drive system configured to translate the mandrel and turn the one or more rollers.

Example 2

The folding device of Example 1, wherein the mandrel is configured to move distally as the one or more rollers fold the sleeve.

Example 3

The folding device of Examples 1 or 2, wherein the one or more rollers are made from polyurethane.

Example 4

The folding device of any one or more of Examples 1 through 3, wherein the one or more rollers include four rollers.

Example 5

The folding device of any one or more of Examples 1 through 4, wherein the one or more rollers are self-righting.

Example 6

The folding device of any one or more of Examples 1 through 5, wherein the drive system is configured to translate the mandrel and turn the one or more rollers in coordination with each other.

Example 7

The folding device of any one or more of Example 1 through 6, wherein the mandrel is configured to translate the retainer as the mandrel translates distally.

Example 8

The folding device of any one or more of Examples 1 through 7, wherein the rate of rotation of the one or more rollers and the rate of translation of the mandrel is electronically controlled.

Example 9

The folding device of any one or more of Examples 1 through 7, wherein the rate of rotation of the one or more rollers and the rate of translation of the mandrel is mechanically geared.

Example 10

The folding device of any one or more of Examples 1 through 7, wherein the rotation of the one or more rollers and the rate of translation of the mandrel is variable.

Example 11

The folding device of any one or more of Examples 1 through 7, wherein the one or more rollers include a plurality of rollers, wherein each roller configured such that the rate of rotation for reach roller is independently controlled.

Example 12

The folding device of any one or more of Examples 1 through 7, wherein the one or more rollers are powered by direct drive.

Example 13

The folding device of any one or more of Examples 1 through 12, wherein at least a portion of the drive system is powered pneumatically.

Example 14

The folding device of any one or more of Examples 1 through 13, wherein the mandrel is configured to receive the retainer in a collapsed configuration.

Example 15

The folding device of any one or more of Examples 1 through 13, wherein the mandrel is configured to receive the retainer in an expanded configuration.

Example 16

The folding device of any one or more of Examples 1 through 15, wherein the mandrel includes a wedge configured to expand the retainer.

Example 17

The folding device of any one or more of Examples 1 through 16, further comprising one or more idle rollers.

Example 18

The folding device of Example 17, wherein the one or more idle rollers are configured to apply pressure to the one or more rollers through the sleeve.

Example 19

The folding device of any one or more of Examples 1 through 18, wherein each roller of the one or more rollers is rotatably coupled to a pivotable arm, wherein each pivotable arm is configured to pivot each respective roller relative to the mandrel.

Example 20

A sleeve folding system comprising: (a) a flexible sterile cover; (b) a retainer, wherein the retainer is has greater rigidity than the cover; and (c) a folding mechanism configured to fold the cover onto the retainer, wherein the folding mechanism includes: (i) a mandrel configured to receive the retainer, (ii) a one or more rollers configured to rotate in contact with the cover, wherein the mandrel is configured to translate the cover relative to the one or more rollers while being folded over the retainer by the one or more rollers, and (iii) a drive system configured to rotate the one or more rollers and translate the mandrel proximally.

Example 21

The system of Example 20, wherein the drive system is configured to rotate the one or more rollers simultaneously with translation of the mandrel.

Example 22

The system of Examples 20 or 21, wherein the drive system is configured to rotate the one or more rollers in correspondence with translation of the mandrel in accordance with a fixed ratio of rotation to translation.

Example 23

The system of any one or more of Examples 20 through 22, wherein the retainer includes an elongate receiving portion, wherein the folding mechanism is configured to fold the cover onto the receiving portion of the retainer.

Example 24

The system of Example 23, wherein the receiving portion of the retainer defines a longitudinal axis, wherein the one or more rollers are configured to rotate about an axis oriented perpendicularly relative to the longitudinal axis of the receiving portion.

Example 25

The system of any one or more of Examples 20 through 24, further comprising a control system, wherein the control system is configured to coordinate rotation of each roller of the one or more rollers with translation of the mandrel.

Example 26

The system of Example 25, wherein the control system includes a plurality of sensors and a controller, wherein the sensors are in communication with the controller such that the sensors are configured to communicate motion data related to the one or more rollers and the mandrel to the controller.

Example 27

The system of Example 26, wherein the plurality of sensors includes an encoder.

Example 28

The system of any one or more of Examples 20 through 27, wherein the drive system includes a roller drive assembly configured to drive each roller of the one or more rollers and a mandrel drive assembly configured to drive translation of the mandrel.

Example 29

The system of Example 28, wherein the one or more rollers includes a plurality of rollers, wherein the roller drive assembly is configured to drive each roller of the plurality of rollers at the same rate of rotation.

Example 30

The system of Example 28, wherein the one or more rollers includes a plurality of rollers, wherein the roller drive assembly is configured to drive rotation of each roller independently of all other rollers.

Example 31

The system of any one or more of Example 28 through 30, wherein each roller is configured to pivot relative to the mandrel, wherein the roller drive assembly is configured to drive rotation of each roller while permitting pivoting of each roller relative to the mandrel.

Example 32

The system of any one or more of Examples 28 through 31, wherein the mandrel drive assembly includes a linear actuator configured to drive the mandrel distally and proximally.

Example 33

The system of Example 32, wherein the linear actuator includes a pneumatic actuator.

Example 34

A method for providing a flexible sterile cover folded on a retainer, the retainer including a proximal end and a distal end, the method comprising: (a) positioning the cover and the retainer onto a mandrel; (b) rotating a plurality of rollers in synchronization with each other relative to the cover to thereby fold the cover onto the retainer; (c) translating the mandrel relative to the plurality of rollers while rotating the rollers.

Example 35

The method of Example 34, wherein the step of positioning includes (i) attaching the retainer onto the mandrel, and (ii) placing a proximal edge of the cover over an exterior surface of the retainer.

Example 36

The method of Examples 34 or 35, further comprising pivoting each roller of the plurality of rollers into contact with the cover.

Example 37

The method of any one or more of Examples 34 through 36, further comprising ejecting the retainer from the mandrel when the cover is substantially folded on the retainer.

Example 38

The method of Example 37, further comprising pivoting each roller of the plurality of rollers away from the cover prior to ejecting the retainer.

Example 39

The method of any one or more of Examples 34 through 38, wherein the step of translating the mandrel is performed at a rate of translation relative to the rollers to avoid binding of the cover on the retainer.

Example 40

A sleeve folding system comprising: (a) a flexible sterile cover; (b) a retainer, wherein the retainer is has greater rigidity than the cover; and (c) a folding mechanism configured to fold the cover onto the retainer, wherein the folding mechanism includes: (i) a drive assembly, (ii) a mandrel extending longitudinally along a rolling axis from the drive assembly and configured to receive the retainer, (iii) a plurality of rollers arranged around the mandrel and configured to relative to the mandrel, and (iv) a positioning assembly, wherein the positioning assembly includes a pivoting arm associated with each roller of the plurality of rollers, wherein the positioning assembly is configured to move each roller of the plurality of rollers towards the mandrel, wherein the drive assembly is configured to move the mandrel along the rolling axis to thereby translate the cover relative to the one or more rollers while being folded over the retainer by the one or more rollers, wherein the drive assembly is further configured to drive rotation of each roller of the plurality of rollers while moving the mandrel along the rolling axis.

IV. MISCELLANEOUS

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A folding device for placing an elastomer thin sleeve on a retainer, the folding device comprising:
    (a) a mandrel configured to translate relative to a portion of the folding device, the mandrel being adapted to releasably receive the retainer;
    (b) one or more rollers configured to rotate relative to the mandrel, the rotation of the one or more rollers being configured to fold the sleeve onto the retainer; and
    (c) a drive system configured to translate the mandrel and turn the one or more rollers.

2. The folding device of claim 1, the mandrel being configured to move distally as the one or more rollers fold the sleeve.

3. The folding device of claim 1, the one or more rollers including polyurethane.

4. The folding device of claim 1, the one or more rollers including four rollers.

5. The folding device of claim 1, the one or more rollers being configured as self-righting rollers.

6. The folding device of claim 1, the drive system being configured to translate the mandrel and turn the one or more rollers in coordination with each other.

7. The folding device of claim 1, the mandrel being configured to translate the retainer as the mandrel translates distally.

8. The folding device of claim 1, the rate of rotation of the one or more rollers and the rate of translation of the mandrel being electronically controlled.

9. The folding device of claim 1, the rate of rotation of the one or more rollers and the rate of translation of the mandrel being mechanically geared.

10. The folding device of claim 1, the rate of rotation of the one or more rollers and the rate of translation of the mandrel being variable.

11. The folding device of claim 1, the one or more rollers including a plurality of rollers, each roller of the plurality of rollers being configured such that the rate of rotation for each roller is independently controlled.

12. The folding device of claim 1, each roller of the one or more rollers being powered by a direct drive.

13. The folding device of claim 1, at least a portion of the drive system being powered pneumatically.

14. The folding device of claim 1, the mandrel being configured to receive the retainer with the retainer being in a collapsed configuration.

15. The folding device of claim 1, the mandrel being configured to receive the retainer with the retainer in an expanded configuration.

16. The folding device of claim 1, the mandrel including a wedge configured to expand the retainer.

17. The folding device of claim 1, further comprising one or more idle rollers, the one or more idle rollers being configured to apply pressure to the one or more rollers through the sleeve.

18. The folding device of claim 1, each roller of the one or more rollers being rotatably coupled to a pivotable arm, each pivotable arm being configured to pivot each respective roller relative to the mandrel.

19. A sleeve folding system comprising:
(a) a flexible sterile cover;
(b) a retainer, the retainer having greater rigidity than the cover; and
(c) a folding mechanism configured to fold the cover onto the retainer, the folding mechanism including:
  (i) a mandrel configured to receive the retainer,
  (ii) one or more rollers configured to rotate while in contact with the flexible sterile cover, the mandrel being configured to translate the flexible sterile cover relative to the one or more rollers while the flexible sterile cover is being folded over the retainer by the one or more rollers, and
  (iii) a drive system configured to rotate the one or more rollers and translate the mandrel.

20. A method for providing a flexible sterile cover folded on a retainer, the retainer including a proximal end and a distal end, the method comprising:
(a) positioning the cover and the retainer onto a mandrel;
(b) rotating a plurality of rollers in synchronization with each other relative to the cover to thereby fold the cover onto the retainer; and
(c) translating the mandrel relative to the plurality of rollers while rotating the rollers.

* * * * *